United States Patent [19]

Kolff

[11] Patent Number: 5,370,640
[45] Date of Patent: Dec. 6, 1994

[54] INTRACORPOREAL CATHETER PLACEMENT APPARATUS AND METHOD

[76] Inventor: Jack Kolff, 1086 Franklin St., Johnstown, Pa. 15905-4305

[21] Appl. No.: 86,137

[22] Filed: Jul. 1, 1993

[51] Int. Cl.$^5$ ............................................... A61B 1/00
[52] U.S. Cl. ............................................ 606/2; 604/21; 604/164; 604/53; 607/88
[58] Field of Search .................. 606/13–16, 606/2, 3; 607/88, 90, 92, 93; 128/657, 772, 6; 604/164–166, 170, 280, 20, 21, 53

[56] References Cited

U.S. PATENT DOCUMENTS

| | | | |
|---|---|---|---|
| 3,123,066 | 1/1960 | Brumley | 607/92 |
| 4,566,438 | 1/1986 | Liese et al. | 606/16 |
| 4,753,637 | 6/1988 | Horneffer | |
| 4,927,412 | 5/1990 | Menasche | |
| 5,021,045 | 6/1991 | Buckberg et al. | 604/53 |
| 5,271,380 | 12/1993 | Riek et al. | 604/164 |

OTHER PUBLICATIONS

"Retrograde Cardioplegia: Detail for Coronary Sinus Canalation Technique" Kit V. Arom, M.D. Robert W. Emery, M.D. Jan. 8, 1992.

Primary Examiner—Stephen C. Pellegrino
Assistant Examiner—Michael Peffley
Attorney, Agent, or Firm—Thorpe, North & Western

[57] ABSTRACT

A fiberoptic stylet apparatus for assisting in the safe and effective intracorporeal placement of catheters comprises an elongate, light-emitting fiberoptic cable coupled to a conventional stylet body in a parallel alignment therewith. The distal extremities of the cable and stylet are positioned adjacent one another. A surgeon inserts the fiberoptic cable/stylet coupling into a catheter in much the same manner as a conventional stylet, so that the adjacent distal extremities reside within the catheter tip. A light source connected to the fiberoptic cable is activated to cause said cable to emit light which passes through the catheter tip. When the surgeon inserts the catheter into the coronary sinus or other body cavity of a patient, the light passes through the translucent tissue surrounding the catheter tip. This permits the surgeon to actually see the position of the catheter tip relative to its organic surroundings and thus enables the surgeon to position the catheter without stretching, tearing or puncturing the walls of the coronary sinus or other delicate objects.

27 Claims, 3 Drawing Sheets

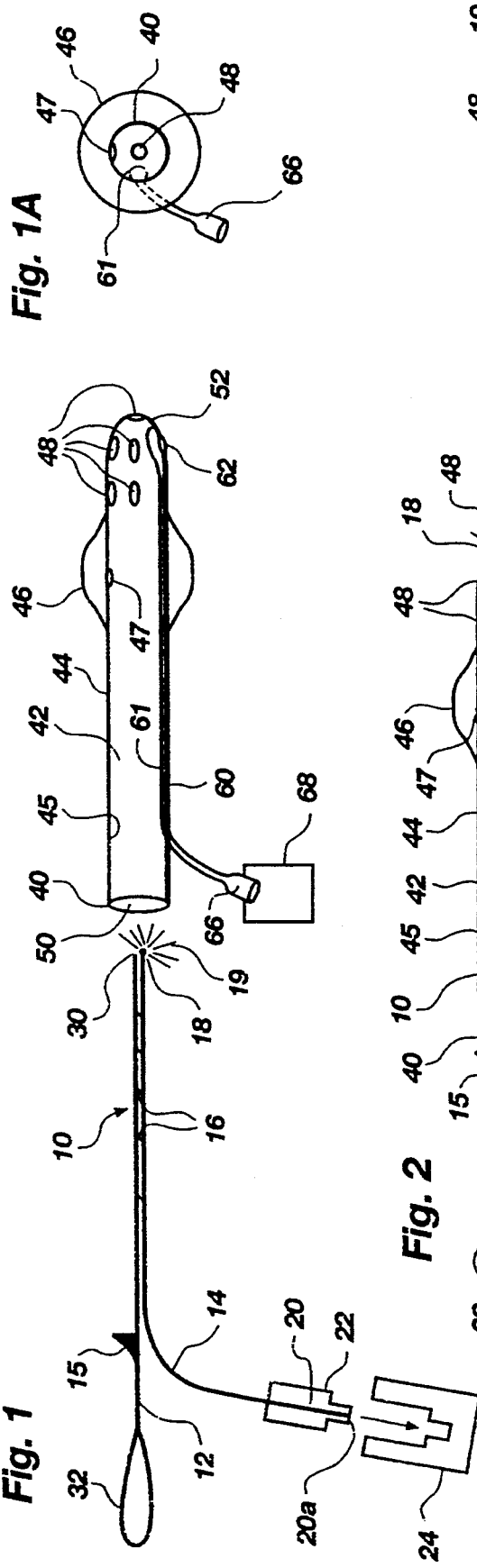
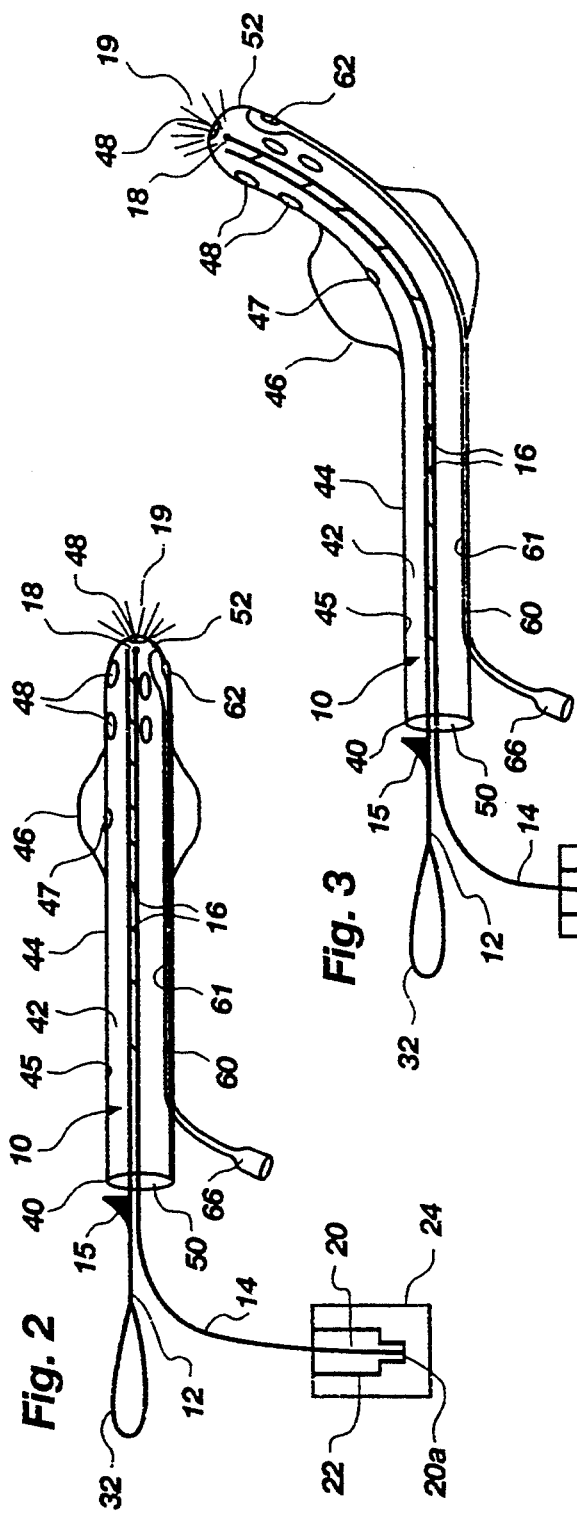

INTRACORPOREAL CATHETER PLACEMENT APPARATUS AND METHOD

BACKGROUND OF THE INVENTION

1. The Field of the Invention

The present invention relates to the safe and effective intracorporeal placement of catheters during cannulation of body cavities. More particularly, it concerns illumination of such cavities by a light-emitting fiberoptic cable for placement within a catheter to enable a surgeon to visually observe the catheter tip relative to its organ surroundings.

2. The Background Art

Catheters are well known in the art for injecting fluid into, or withdrawing fluid from, a vein of a patient. Catheters can also be introduced into other cavities or organs of the human body such as the coronary sinus and atria during cardiopulmonary bypass and other open heart surgery procedures. Of current interest are apparatus and methods for quickly and safely placing a flexible catheter within the coronary sinus for infusing a chemical fluid into the heart to temporarily stop and nourish the heart during heart surgery.

It has long been recognized that in order to provide the best surgical conditions during heart surgery, it is necessary to stop the normal operation of the heart and interrupt the blood supply to the heart muscle. A pulsating heart consumes a large amount of oxygen and therefore requires much more energy than an arrested heart. However, even the resting heart needs an oxygen and nutritional supply no keep its muscle cells alive. When the cardiac muscle cells fail to receive enough oxygen the deficiency causes serious damage in the form of perioperative (during or within 24 hours after the surgical procedure) myocardial necrosis (death of the heart tissue). The consequences of myocardial necrosis range from low cardiac blood output to death of the patient. For these and other reasons not specifically discussed, one of the primary goals of myocardial preservation techniques during heart surgery is to stop the heart to thereby reduce myocardial oxygen consumption and thus decrease the risks of oxygen deficiency.

It is well known that stopping the electromechanical work of the heart significantly reduces myocardial oxygen consumption. During heart surgery, the patient's heart can be stopped and the functions thereof taken over by a heart-lung machine. Many methods have been developed to stop the heart during heart surgery to thereby reduce the oxygen and energy requirements of the heart and thus avoid the risk of myocardial necrosis. The most advantageous method used to date is the infusion of a continuous flow of cold cardioplegic fluid to cool and stop the beating of the heart, known as cardioplegia ("heart stop"). Cardioplegic solutions are typically cooled fluids containing potassium, magnesium procaine, or a hypocalcemic composition. In stopping the heart, care must be taken to prevent the heart muscle from continuing to beat without blood being supplied thereto in order to avoid myocardial necrosis.

Cardioplegic fluids for stopping the heart are delivered either directly or indirectly into the coronary arteries or into the coronary sinus (a large vein of the heart through perfusion catheters. Perfusion catheters typically comprise dual tubes coupled together in substantially a parallel alignment. A surgeon grips the catheter by its proximal end and inserts its distal end into the coronary sinus. A selectively inflatable balloon circumscribes the catheter near its distal end and blocks the coronary sinus. One of the tubes is connected at its proximal end to a fluid source and thereby introduces cardioplegic fluid into the coronary sinus. The other tube communicates with the coronary sinus at its distal end and is often connected to a pressure sensor at its proximal end to thereby provide a pressure reading of the coronary sinus. Perfusion (the passage of a fluid over or through the vessels of an organ or tissue) is used to deliver cardioplegia in an antegrade manner (through arteries in the normal direction of blood flow), in a retrograde manner (through veins opposite the normal blood flow direction), or in a combination of antegrade and retrograde delivery.

In retrograde cardioplegia, an old procedure repopularized recently, it is known to insert a balloon catheter through a small incision in the right atrium and then advance the catheter into the coronary sinus. A self inflated or hand inflated balloon stops the normal fluid flow into the right atrium. The cardioplegic solution is then perfused backwards through the coronary veins to the heart, i.e. in a direction reversed to that of normal blood flow. The catheter remains in position throughout the operation in order to periodically readminister the cardioplegic solution. Retrograde cardioplegia is more complicated than antegrade cardioplegia but is often preferred in order to avoid the problems of antegrade delivery, which include: encumbering the limited operative field by the insertion of perfusion catheters directly into the coronary arteries; aortic insufficiency; and nonhomogeneous cooling and cardioplegic maldistribution of areas of the heart downstream from coronary artery obstructions.

It is of life threatening importance that the catheter be properly placed during retrograde cardioplegia. It is suggested that the tip of the catheter be approximately 1 to 2 centimeters from the left atrial appendage. Kit V. Arom, M.D. and Robert W. Emery, M.D., "Retrograde Cardioplegia: Detail for Coronary Sinus Cannulation Technique," 53 Ann. Thorac. Surg., 714–15 (1992). However, the process of properly placing the catheter poses additional risks to the patient. The surgeon must advance the catheter by hand into the coronary sinus to a desired location. If the catheter is under-inserted, the cardioplegic fluid will not be perfused at the desired location and the heart will not receive sufficient oxygenated nutrients, increasing the risk of a failed operation or even myocardial necrosis as discussed above. If the catheter is over-inserted, it may damage the walls of the atrium or the coronary sinus in addition to providing fluid to the wrong location in the organ. This risk arises because the atria and the coronary sinus are made from particularly fragile tissues which tear easily when probed by a catheter.

Control of insertion depth is also important to fully block the coronary sinus after the catheter has been inserted in order to prevent the cardioplegic solution from flowing backward from the coronary sinus into the right atrium. While proper catheter placement is of life-threatening importance in retrograde cardioplegia, it is always important regardless of the particular procedure or operation being performed.

The generally accepted method for confirming proper catheter placement during retrograde cardioplegia has depended upon costly trial and error: the surgeon essentially guides the catheter into the coronary sinus by feel. The surgeon holds a flexible catheter with a stylet in place in the left hand and inserts it into the right atrium anterior to the venous cannula. The surgeon's right hand is placed along the heart's diaphragmatic surface. The surgeon places the index finger at the inferior vena cava and atrioventricular groove junction to locate the catheter tip and gently guide it into the coronary sinus and greater cardiac vein. The surgeon further advances the flexible catheter forward, and manually palpates the inflatable balloon. If the palpations are not felt, it is certain that the catheter is not in place and most likely is in either the right ventricle or inferior vena cava. Arom, "Retrograde Cardioplegia" at 714. The surgeon must then withdraw the catheter and repeat the procedure until proper placement is achieved. This trial and error approach takes precious time away from the rest of the surgery and results in undue risk to the patient's internal body cavities.

In short, the generally accepted method of physically confirming proper catheter placement during retrograde cardioplegia has many disadvantages. One serious disadvantage is that the surgeon cannot see or confirm with absolute certainty that the catheter is in the right place, but must feel to determine proper catheter placement. Not only is this generally accepted method tedious and risky, but it requires the catheters and stylii to be limited to softer material to minimize the risk of injury to the veins and the organ walls. The surgeon is thus caught up in a classic conflict situation: soft structure is needed to protect against puncture, and stiff structure is needed to enable the surgeon to feel for the location of the catheter.

There is thus a great need to minimize the risks of intracorporeal catheter placement, especially for retrograde cardioplegia. U.S. Pat. No. 4,927,412 attempts a solution to this problem by teaching a catheter having a depth control flange coupled to the catheter at a predetermined distance from the catheter tip to prevent the catheter from being over-inserted. The flange comprises a disc made of a soft plastic material which prevents over-insertion when the flange engages the wall of the right atrium while the tip of the catheter protrudes into the coronary sinus. Although this approach does provide protection against over-insertion, the surgeon still cannot see or confirm with absolute certainty that the catheter is in the right place. This approach thus fails to significantly limit the risks of undue wearing or tearing of the coronary sinus and right atrium walls, and still does not preclude over-insertion because the surgeon cannot see the position of the catheter tip relative to its organic surroundings.

Although the industry continues to research methods and devices for assisting in the proper intracorporeal placement of catheters, none of the methods or devices known to applicant involve a self-contained catheter apparatus which enables the surgeon to actually see the position of the catheter tip relative to the delicate walls of the body cavities and organs. It is clear that there is a need for a catheter positioning apparatus and method which not only allows greater flexibility in choosing among the use of softer or stiffer catheter materials, but which also allows the surgeon to actually see and observe the position of the catheter tip relative to its organic surroundings.

OBJECTS AND SUMMARY OF THE INVENTION

It is therefore an object of the present invention to provide a fiberoptic stylet apparatus for assisting in the proper intracorporeal placement of catheters.

It is an additional object of the invention no provide such a fiberoptic stylet apparatus which makes the intracorporeal placement of catheters simpler and easier to achieve.

It is another object of the invention to provide such a fiberoptic stylet apparatus which significantly minimizes the threat of tearing, puncture and other damage to internal veins and organ walls during the intracorporeal placement of catheters.

It is also an object of the invention to provide such a fiberoptic stylet apparatus which allows the user to see the position of a catheter tip relative to its organic surroundings by transillumination of the delicate vessel wall.

While the present invention is described in terms of a catheter to be used in retrograde cardioplegia solution administration in the coronary sinus during heart surgery, it is to be understood that the subject fiberoptic stylet apparatus and method may be used in any field of catheter application. Those having ordinary skill in the field of this invention will appreciate the advantages of the invention, and its application to a wide variety of catheter uses.

The above objects and others not specifically recited are realized in a specific illustrative embodiment of a fiberoptic stylet apparatus for assisting in the safe intracorporeal placement of clear plastic and other light-transmitting catheters. The fiberoptic stylet apparatus includes a conventional elongate stylet body having a proximal end for gripping and a distal end for inserting into the catheter tip. The stylet is essentially a pliable guide wire capable of retaining a curved shape or other deformation. At least one elongate flexible fiberoptic cable is coupled to the stylet body in parallel alignment therewith such that the distal end of the fiberoptic cable is positioned adjacent to the distal end of the stylet body. The fiberoptic cable is connected at its proximal end to a light source which introduces light therein, causing the cable to carry the light and emit it from the distal end thereof.

In use, the surgeon shapes the stylet/cable coupling into a predetermined curve at the distal end and inserts it into a soft, flexible catheter so that the adjacent distal ends of the stylet body and fiberoptic cable are positioned within the catheter tip. The stylet holds the assembly in the predetermined curved shape. The light source is activated so that light passes from the distal end of the fiberoptic cable through the catheter tip. The tip of the catheter is inserted into a patient at a desired location. Because of the translucent quality of human tissue, the light emitted from the catheter illuminates and passes through the catheter's organic surroundings to enable the surgeon to observe the location of the catheter tip relative to said organic surroundings. This allows the surgeon to safely guide the catheter to a desired intracorporeal location while actually viewing the tip relative its environment and thus eliminating the need to guide the catheter by feel and guess work.

BRIEF DESCRIPTION OF THE DRAWINGS

The above and other objects, features and advantages of the invention will become apparent from a consideration of the subsequent detailed description presented in connection with the accompanying drawings in which:

FIG. 1 is a side perspective view of a catheter with a fiberoptic stylet apparatus made in accordance with the principles of the present invention;

FIG. 1A is a front, end view of the catheter shown in FIG. 1;

FIG. 2 is a side perspective view of the fiberoptic stylet apparatus of FIG. 1 inserted within the catheter;

FIG. 3 is a side perspective view of the inserted fiberoptic stylet apparatus of FIG. 2 in a predetermined curved configuration;

Figure 4:
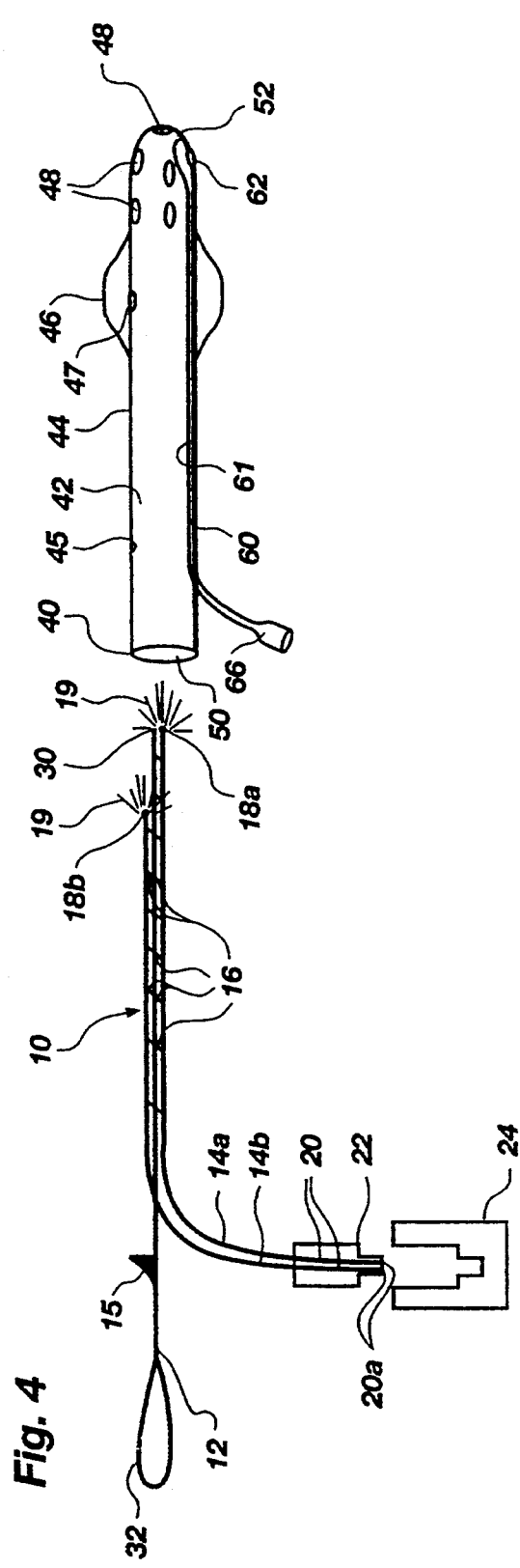
FIG. 4 is a side perspective view of an alternative embodiment of the fiberoptic stylet apparatus of FIG. 1.

DETAILED DESCRIPTION OF THE PRESENTLY PREFERRED EMBODIMENTS OF THE PRESENT INVENTION

Reference will now be made to the drawings wherein like structures will be provided with like reference numerals.

Referring to FIGS. 1-3, there is shown a fiberoptic stylet apparatus, generally designated at 10, for insertion within a conventional clear plastic catheter 40. The fiberoptic stylet 10 comprises an elongate, flexible fiberoptic cable 14 coupled to a conventional, elongate stylet body 12 in a substantially parallel alignment therewith. The coupling structure, illustrated at 16, will typically comprise glue, tape or some other suitable bonding agent. When coupled as such, the fiberoptic cable 14 and the styler 12 will be referred to collectively hereafter as fiberoptic styler 10. The cable 14 may alternatively be coupled to the styler 12 in a helical or other non-parallel configuration.

The conventional stylet 12 has been used in the art for inserting within a flexible catheter to keep it rigid. In the present invention, the stylet 12 serves the additional purpose of advancing the fiberoptic cable 12, to which it is coupled, into the tip 52 of the catheter 40 to allow said fiberoptic cable to emit light through the catheter tip.

The stylet 12 is a pliable, semi-rigid metal wire and includes a distal end 30 for insertion into the catheter tip 52, a proximal end 32 which acts as a handle, and a stylet shoulder 15 for preventing the distal end 30 from protruding through the catheter tip 52. Any of the alternative means which exist in the art for preventing protrusion of the distal end 30 through the catheter tip 52 can be used with the present invention, such as a substantially closed catheter tip (not shown). The proximal end 32 may comprise a loop as in FIGS. 1-7 as well as a free end or any other shape or configuration. The stylet 12 can be made of any metal capable of being shaped into and retaining a predetermined curved deformation as shown in FIG. 3. Referring to FIG. 3, the curved stylet holds the catheter 40 in a curved shape for quickly and accurately inserting the catheter into curved body cavities, veins and the like, and thereby minimizes stretching and damage to the walls of the body cavity. The stylet 12 may embody any desired cross-sectional shape and could be made of any material capable of being formed into an elongate semi-rigid wire having a thickness of about 0.15 cm, or any smaller or larger thickness which would satisfy the purpose of the present invention.

The fiberoptic cable 14 shown in FIGS. 1-3 includes a distal end 18 for inserting into the catheter tip 52, and a proximal end 20 to which light connection means or plug 22 is attached. The light plug 22 encapsulates the proximal end 20 such that a light-introducing means or tip 20a thereof is exposed. When the light plug 22 is inserted into a light source 24, the light-introducing means or tip 20 a contacts and receives light therefrom which is carried to and emitted from the distal end 18. The light connection means or plug 22 may also comprise any other connector configuration capable of removably joining a cable to a source, and may be made from any suitable synthetic polymer or other non-conductive material.

The flexible catheter 40 in FIGS. 1-7 is for inserting within a body cavity such as the coronary sinus and includes a substantially cylindrical, light-transmitting wall 44 having an inner surface 45. Also included are a selectively inflatable balloon 46 for selectively blocking the coronary sinus, perfusion apertures 48 for infusing liquid solution through the coronary sinus and veins, an entrance 50 for receiving the fiberoptic styler 10, and a tip 52. The balloon 46 may be either self inflating, or manually inflatable. The light-transmitting wall 44 is typically made of clear plastic, but may alternatively be made of any transparent or translucent material, or any other preferably flexible material penetrable by light.

The catheter 40 further comprises a dual lumen catheter. The balloon 46 is in fluid communication with a first lumen 42 through at least one slot 47. The first lumen 42 is for injecting fluid through the perfusion apertures 48 into a body cavity, and a second lumen 60 comprises a proximal port 66 for attachment to a pressure sensor 68. The pressure sensor 68 is used for sensing the pressure at a distal port 62. The second lumen 60 is located within the first lumen 42 and comprises a channel wall 61 bonded to the inner surface 45 of the cylindrical wall 44. The first and second lumen 42 and 60 could alternatively comprise separate tubular members, the second such lumen being coupled to the inner surface of the first such lumen. One having ordinary skill in this field will appreciate that the scope of the present invention includes many different embodiments of the catheter 40.

The flexible fiberoptic cable 14 of FIGS. 1-3 (14a-b in FIG. 4) is coupled to the stylet 12 as mentioned above to form the fiberoptic stylet 10. The fiberoptic cable 14 is thus placed within the catheter 40 simultaneously with the stylet 12. When the fiberoptic stylet 10 is inserted into the catheter, the distal end 18 of the fiberoptic cable 14 is preferably within ¼" from the very end of the catheter tip 52. Since the purpose of the cable 14 is to illuminate the area directly surrounding the catheter tip 52 with its distal end 18, the closer its distal end is to the catheter tip, the better the illumination is of said surrounding area. Accordingly, the distal end 18 of the fiberoptic cable 14 is preferably positioned slightly in front of the distal end 30 of the stylet 12 so as to be inserted as far into the tip 52 as possible. The distal end 18 of the fiberoptic cable 14 may alternatively be positioned even with, or slightly behind, the distal end 30 of the stylet 12.

The fiberoptic cable 14 comprises a single strand of ultrapure, transparent optical fiber, or a bundle of such fibers, whose refraction properties allow light to be transmitted around curves. It may also comprise any other flexible material capable of carrying light and may be coupled to the stylet 12 by gluing, taping or in any other manner known to those skilled in the relevant art. The cable 14 includes a coating or some other light-entrainment structure (not shown) upon its exterior surface, and care should be taken to avoid damaging any such structure when bonding the cable 14 to the stylet 12. Damage to the light-entrainment structure could result in light escaping through the damaged area and would thus frustrate the purposes of the invention.

As mentioned previously, the light source 24 introduces light into said cable 14 which carries the light and emits it from the distal end 18. The light source 24 may comprise any of the different constructs generally known in the art, such as a conventional source for fiberoptic apparatus. The light source 24 may also comprise a portable, battery-operated pen light or vessel light which operates separately and independent of any head lamp or other source and thus permits greater mobility and convenience.

A preferred embodiment of the present invention is illustrated in FIG. 4 and includes a first fiberoptic cable 14a and a second fiberoptic cable 14b coupled in a substantially parallel alignment to the styler 12, as illustrated by the coupling structure at 16. The first fiberoptic cable 14a includes a distal end 8a which is preferably positioned slightly in front of the distal end 30 of the stylet 12. The second fiberoptic cable 14b includes a distal end 18b which is typically positioned somewhat behind the distal end 30 of the stylet 12 as shown in FIG. 4. The advantage of having two light-emitting fiberoptic cables instead of one is additional light; and hence, additional visibility for the surgeon.

The first and second fiberoptic cables 14a and 14b are attached to the connection means 22 for connection to the light source 24. The light source 24 introduces light into the first and second fiberoptic cables 14a and 14b such that light is emitted from the distal ends 18a and 18b of said fiberoptic cables, as illustrated at 19.

It is to be understood that the distal ends 18a and 18b of the first and second fiberoptic cables 14a and 14b may be positioned anywhere with respect to the distal end 30 of the stylet 12 that will enhance the purpose and objects of the present invention. The fiberoptic stylet 10 may thus comprise an infinite number of different embodiments, such as that having first and second fiberoptic cables 14a and 14b as in FIG. 4, a single fiberoptic cable as in FIGS. 1–3, or any number of fiberoptic cables in any number of positions which will accomplish the purpose and objects of the present invention.

In use, a surgeon connects cables 14a–b to the light source 24, forms the light-emitting fiberoptic styler 10 into a predetermined curve and inserts it into the flexible catheter 40. The fiberoptic stylet 10 holds the catheter 40 in the curved shape. The refraction properties of the fiberoptic cables 14a–b permit them to transmit light around the curve to their tips 18a–b, respectively. During heart surgery, the surgeon inserts the catheter into the coronary sinus through a small incision made in the right atrium. Although the tip 52 of the catheter 40 is hidden from view, the light emitted from the distal ends 18a–b of the fiberoptic cables 14a–b penetrates the catheter wall 44 at the tip 52 and thereby illuminates the catheter's translucent organic surroundings such as the walls of the coronary sinus, the walls of the atrium and so forth.

The light and the illuminated organic surroundings are visible to the surgeon, which enables the surgeon to observe the location of the catheter tip 52 relative to said organic surroundings and safely guide the catheter 40 to a desired intracorporeal location, i.e. without puncturing, wearing upon or otherwise damaging the coronary sinus walls, the atrium walls or other delicate intracorporeal objects. The embodiment of FIG. 4 showing two fiberoptic cables 14a–b is a preferred embodiment because it provides more light, and thus more visibility to the surgeon, than an embodiment having only one fiberoptic cable 14 as in FIGS. 1–3. This embodiment is, however, more expensive to manufacture because of the additional fiberoptic cable.

The fiberoptic styler 10 is withdrawn and cardioplegic solution is perfused from the first lumen 42 through the perfusion apertures 48 into the coronary sinus and backwards through the coronary veins to the heart to thereby arrest the pulsating of the heart and thus temporarily reduce or eliminate its oxygen requirements. The catheter remains in place throughout the surgery in order to periodically readminister the cardioplegic solution.

A pressure sensor 68 in communication with the second lumen 60 is well known in the art, and may be used as a secondary aid to proper catheter placement in that a pressure reading of 20 mm Hg indicates a high probability that the catheter tip is in proper position within the coronary sinus, whereas pressure readings of less than 5 mm Hg or greater than 50 mm Hg indicate improper or even dangerous placement. However, the advantages of the visibility offered by the present invention render the pressure sensor 68 optional.

Figure 5:
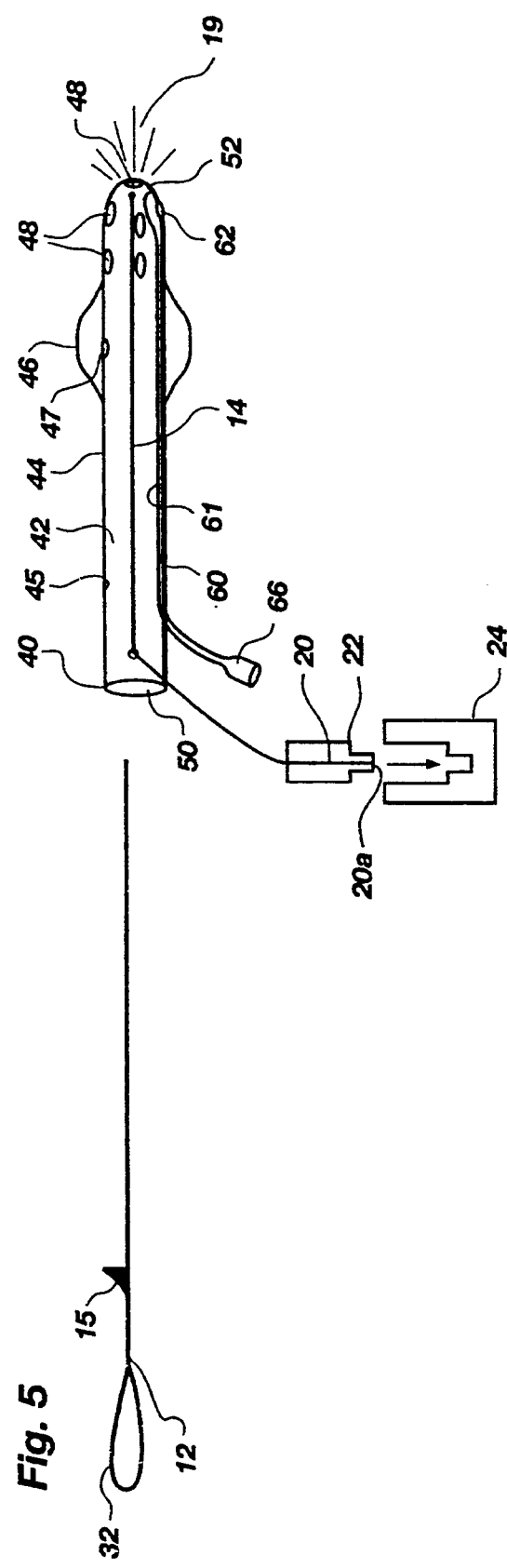
FIG. 5 is a side perspective view of another alternative embodiment of the fiberoptic stylet apparatus of FIG. 1.

It has been found that the closer the light-emitting distal end of the fiberoptic cable is to the translucent walls of the coronary sinus (or other body cavity), the more light passes through said walls, and thus the more visibility the surgeon has of the catheter tip 52 relative to its surroundings. This further increases the accuracy of the surgeon's judgment regarding the placement of the catheter. Accordingly, FIG. 5 illustrates a preferred embodiment of the present invention wherein the fiberoptic cable 14 and the stylet 12 are separate and unconnected. The fiberoptic cable 14 is disposed along the catheter wall 44, and the light emission 19 thereof is thus much closer to the coronary sinus wall during use than if the light emission 19 occurred in the center of the catheter tip 52 as in FIGS. 1–4. The cable 14 is preferably disposed parallel to the catheter 40, but may alternatively be disposed about the catheter wall 44 in a helical or other non-parallel configuration. In this embodiment the fiberoptic cable 14 could either be secured within a secondary lumen, or simply encapsulated within the catheter wall 44 during the fabrication process. The fiberoptic cable 14 will typically be immovably disposed along the catheter wall 44, but the scope of the invention also covers a fiberoptic cable 14 that is removably disposed along the catheter wall 44.

Another advantage to the embodiment of FIG. 5 is that the fiberoptic cable 14 remains with the catheter 40 at all times, even after the stylet 12 is withdrawn to enable delivery of cardioplegic fluid. This allows the surgeon the option of activating the light emission 19 to reconfirm that the catheter 40 is properly positioned, without reinserting the stylet 12. This saves the precious time and effort that would be required to reinsert the stylet 12 during the pressure of surgery.

Figure 6:
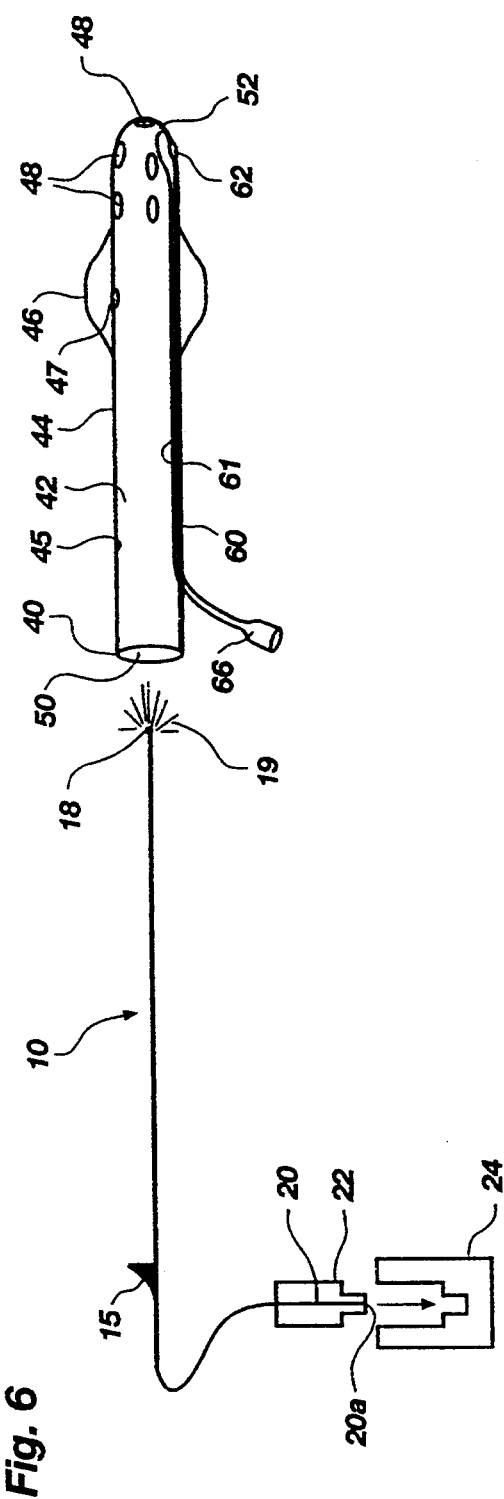
FIG. 6 is a side perspective view of yet another alternative embodiment of the fiberoptic styler apparatus of FIG. 1.

FIG. 6 illustrates yet another embodiment of the present invention. A fiberoptic cable (or bundle) having sufficient rigidity to retain its shape when deformed into some curved configuration, and sufficient strength to guide the catheter 40 to a desired intracorporeal location, could itself function as the styler as well as a light emitter. This is illustrated by a fiberoptic stylet 10 in FIG. 6 which comprises a semi-rigid fiberoptic cable. The fiberoptic stylet 10 is thus a single member and operates identically to the embodiments of FIGS. 1-4. This embodiment advantageously allows for fewer structural members and the consequent cost savings and other advantages thereof which those having ordinary skill in the art will appreciate.

Figure 7:
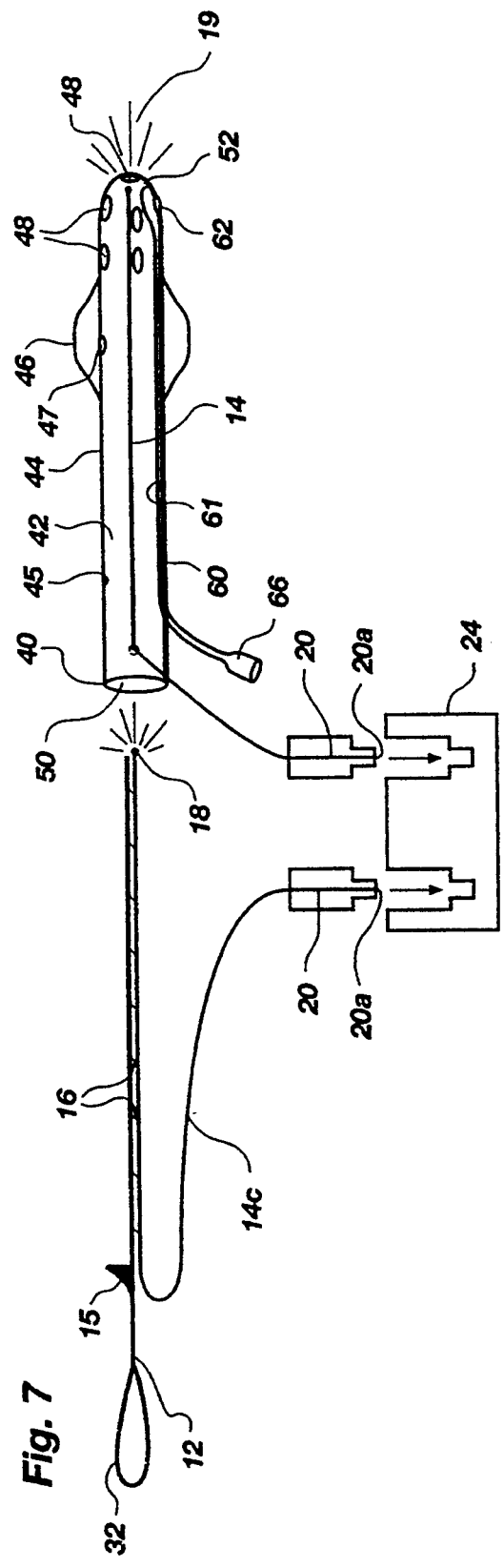
FIG. 7 is a side perspective view of still another alternative embodiment of the fiberoptic stylet apparatus of FIG. 1.

Another preferred embodiment of the present invention is illustrated in FIG. 7, wherein is shown the combined embodiments of FIGS. 1 and 5. In FIG. 7 a first fiberoptic cable 14c is coupled to the stylet 12 as in FIG. 1, and a second fiberoptic cable 14d is disposed along the catheter wall 44 as in FIG. 5. This embodiment thus offers light emissions 19 from both the catheter wall 44 and from inside the catheter tip 52. Again, additional light increases the surgeon's visibility of the catheter tip location, and thus increases his or her ability to place the catheter safely.

The present invention represents a significant advance over traditional apparatus and methods of catheter placement. It is noted that many of the advantages of the present invention accrue due to the placement of a light-transmitting fiberoptic cable within a traditional flexible catheter. The problems associated with quickly and safely placing a catheter within a patient, particularly a perfusion catheter for retrograde delivery of cardioplegic fluid during heart surgery, are overcome to a significant degree by the light-bearing fiberoptic cable. Although the prior art apparatus and methods for catheter placement provide some capacity for proper catheter placement in the form of placement by feel and depth control flanges, the light-bearing structure of the present invention significantly increases both quickness and safety without complicating or encumbering the limited operative field involved in surgeries such as heart surgery. An added advantage offered by the present invention is the capacity to permit the surgeon to actually see the position of the catheter relative to the inner organ walls, veins and so forth, which, without the present invention, would be hidden from view. Those skilled in the art will appreciate from the preceding disclosure that the objectives stated above are advantageously achieved by the present invention.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. An elongate catheter for performing retrograde cardioplegia by delivering a cardioplegic solution into the coronary sinus of the heart, said catheter having a light-transmitting tip, the catheter comprising:
    a flexible catheter body configured and dimensioned insertion into the coronary sinus of the heart, said catheter body including a rounded, light-transmitting tip;
    an elongate stylet body having a proximal end for grasping and a distal end for selectively and removably inserting into the catheter body so that said distal end may be positioned within the tip of the catheter body to thereby enable a user to guide the catheter body to a desired intracorporeal location within the coronary sinus by grasping and maneuvering the styler body;
    at least one elongate fiberoptic cable having a tip which includes a light-emitting fiberoptic terminal face, the cable including means for coupling the cable to the styler body such that said cable tip is positioned adjacent to the distal end of the stylet body and thus within the tip of the catheter body when the distal end of the stylet is positioned therein; and
    means for introducing light into the fiberoptic cable to thereby cause said cable to emit light from the tip thereof so that when the stylet is inserted into the catheter body and the catheter is guided to an intracorporeal location within the coronary sinus, the emitted light penetrates the tip of the catheter body to illuminate said catheter tip and its organic surroundings such that said light is readily visible to a naked, unaided eye of a user and thus enables the user to observe the location of the tip of the catheter body relative to said organic surroundings to thereby safely guide the catheter to a desired intracorporeal location.

2. A catheter as in claim 1 wherein the catheter is configured for insertion within a coronary sinus of a heart.

3. A catheter as in claim 2:
    wherein the stylet is semi-rigid such that a user may shape it into a stable, predetermined curved configuration, the stylet thereby holding the fiberoptic cable in said curved configuration;
    wherein the fiberoptic cable includes refraction properties which allow said cable to transmit the light introduced therein around the curve to thereby emit said light from the tip of said fiberoptic cable; and
    wherein the catheter is made of flexible material configured to receive said curved styler and fiberoptic cable and to be shaped thereby into said predetermined curved configuration for quick and accurate insertion within the coronary sinus through a small incision made in an atrial portion of a heart.

4. A catheter as in claim 1 wherein the catheter further comprises a dual lumen, retrograde perfusion catheter.

5. A catheter as in claim 1 wherein at least a portion of the wall of the catheter is transparent to thereby enable the emitted light to penetrate said portion of the wall.

6. A catheter as in claim 1 wherein at least a portion of the wall of the catheter is translucent to thereby enable the emitted light to penetrate said portion of the wall.

7. A catheter as in claim 1 wherein the tip of the fiberoptic cable is positioned adjacent to and in front of the distal end of the stylet body.

8. A catheter as in claim 1 wherein the catheter is configured for perfusion purposes, the catheter having at least one perfusion aperture located in the tip thereof for introducing fluids into a cavity of the body.

9. A catheter as in claim 1 wherein the fiberoptic cable is coupled to the stylet in substantially a parallel alignment therewith.

10. A catheter as in claim 1:
   wherein the fiberoptic cable has an end distal to the tip and including a terminal face for connection to a light source; and
   wherein the means for introducing light comprise said terminal face of the distal end of the fiberoptic cable, such that when said terminal face is connected to the light source, said light source conveys light into the fiberoptic cable through said terminal face.

11. A catheter as in claim 1 wherein the fiberoptic cable comprises a first fiberoptic cable, the apparatus further comprising:
   a second fiberoptic cable having a tip and including means for coupling said second fiberoptic cable to the stylet body such that said second cable tip is positioned behind the distal end of the stylet body; and
   means for introducing light into the second fiberoptic cable to thereby cause said second cable to emit light from the tip thereof so that the first and second fiberoptic cables collectively illuminate the organic surroundings of a catheter guided to an intracorporeal location.

12. A catheter as in claim 11 wherein the second fiberoptic cable is coupled to the stylet in substantially a parallel alignment therewith.

13. An elongate, tubular catheter for performing retrograde cardioplegia by delivering a cardioplegic solution into the coronary sinus of the heart, said catheter having a light-transmitting tip, the catheter comprising:
   a flexible catheter body configured and dimensioned for insertion into the coronary sinus of the heart, said catheter body including a rounded, light-transmitting tip;
   a stylet body comprising at least one fiberoptic cable having sufficient rigidity to guide the catheter body, said stylet body having a proximal end for grasping, and a distal end including a light-emitting fiberoptic terminal face, the stylet body being configured for selectively and removably inserting into the catheter body so that said distal end is positioned within the tip of the catheter body as a light-emitting source to thereby enable a user to visually detect the light and guide the catheter body to a desired intracorporeal location by grasping and maneuvering the stylet body; and
   means for introducing light into the fiberoptic stylet body to thereby cause said stylet to emit light from the distal end thereof so that when said stylet is inserted into the catheter body and the catheter is guided to an intracorporeal location within the coronary sinus, the emitted light penetrates the tip of the catheter body to illuminate said catheter tip and its organic surroundings such that said light is readily visible to naked, unaided eye of a user and thus enables the user to observe the location of the tip of the catheter body relative to said organic surroundings to thereby safely guide the catheter to a desired intracorporeal location.

14. An elongate catheter for performing retrograde cardioplegia by delivering a cardioplegic solution into the coronary sinus of the heart, said catheter having a light-transmitting tip, the catheter comprising:
   a flexible catheter body configured and dimensioned for insertion into the coronary sinus of the heart, said catheter body including a rounded, light-transmitting tip;
   an elongate stylet body having a proximal end for grasping and a distal end for selectively and removably inserting into the catheter body so that said distal end may be positioned within the tip of the catheter body to thereby enable a user to guide the catheter body to a desired intracorporeal location within the coronary sinus by grasping and maneuvering the stylet body;
   at least one elongate fiberoptic cable having a tip and disposed along a wall of the catheter such that said cable tip is incorporated within the catheter wall at the tip of the catheter body;
   means for introducing light into the fiberoptic cable to thereby cause said cable to emit light from the tip thereof so that when the stylet is inserted into the catheter body and the catheter is guided to an intracorporeal location within the coronary sinus, the emitted light penetrates the tip of the catheter body to illuminate said catheter tip and its organic surroundings such that said light is readily visible to a naked, unaided eye of a user and thus enables the user to observe the location of the tip of the catheter body relative to said organic surroundings to thereby safely guide the catheter to a desired intracorporeal location.

15. A catheter as in claim 14 wherein the catheter is configured for insertion within a coronary sinus of a heart.

16. A catheter as in claim 15:
   wherein the styler is semi-rigid such that a user may shape it into a stable, predetermined curved configuration;
   wherein the fiberoptic cable includes refraction properties which allow said cable to transmit the light introduced therein around the curve to thereby emit said light from the tip of said fiberoptic cable; and
   wherein the catheter is made of flexible material configured to receive said curved stylet and to be shaped thereby into said predetermined curved configuration for quick and accurate insertion within the coronary sinus through a small incision made in an atrial portion of the heart.

17. A catheter as in claim 14 wherein the catheter further comprises a dual lumen, retrograde perfusion catheter.

18. A catheter as in claim 14 wherein at least a portion of the wall of the catheter is transparent to thereby enable the emitted light to penetrate said portion of the wall.

19. A catheter as in claim 14 wherein at least a portion of the wall of the catheter is translucent to thereby enable the emitted light to penetrate said portion of the wall.

20. A catheter as in claim 14 wherein the tip of the fiberoptic cable is positioned adjacent to and in front of the distal end of the stylet body when said stylet body is inserted into the catheter.

21. A catheter as in claim 14 wherein the catheter is configured for perfusion purposes, the catheter having at least one perfusion aperture located in the tip thereof for introducing fluids into a cavity of the body.

22. A fiberoptic stylet apparatus as in claim 14 wherein the fiberoptic cable comprises a first fiberoptic cable, the apparatus further comprising:

- at least a second fiberoptic cable having a tip and including means for coupling said at least a second fiberoptic cable to the stylet body such that said second cable tip is positioned near the distal end of the stylet body;
- wherein the means for introducing light are also for introducing light into the second fiberoptic cable to thereby cause said second cable to emit light from the tip thereof so that the first and second fiberoptic cables collectively illuminate the organic surroundings of a catheter guided to an intracorporeal location.

23. A catheter as in claim 22 wherein the second fiberoptic cable is coupled to the stylet in substantially a parallel alignment therewith.

24. A method for assisting in the safe intracorporeal placement of an elongate catheter having a light-transmitting tip within the coronary sinus of the heart during retrograde cardioplegia, the method comprising the steps of:

- a) selecting an elongate stylet body having a proximal end and a distal end;
- b) coupling at least one elongate fiberoptic cable having a tip to the stylet body such that said cable tip is positioned adjacent to the distal end of the stylet body;
- c) illuminating the fiberoptic cable with means for introducing light into the fiberoptic cable to thereby cause said cable to emit light from the tip thereof;
- d) inserting the stylet, and thus the fiberoptic cable coupled thereto, into a flexible catheter body having a light-transmitting tip such that the distal end of the stylet and the adjacent tip of the fiberoptic cable are positioned within the tip of the catheter body;
- e) inserting the catheter body into the coronary sinus of the heart so that the emitted light penetrates the tip of the catheter to illuminate said tip and its organic surroundings such that said light is readily visible to a naked, unaided eye of a user and thus enables the user to observe the location of the tip of the catheter relative to said organic surroundings; and
- f) maneuvering the catheter body within the coronary sinus while observing the location of the tip of the catheter body relative to said organic surroundings to thereby safely guide the catheter to a desired intracorporeal location within said coronary sinus.

25. A method according to claim 24 wherein the step of coupling further comprises coupling at least one said elongate fiberoptic cable to the stylet body in substantially a parallel alignment therewith.

26. A method according to claim 24 wherein the fiberoptic cable comprises a first fiberoptic cable, the method further comprising the following steps:

- j) coupling a second fiberoptic cable having a tip to the stylet body such that said second cable tip is positioned behind the distal end of the stylet body; and
- k) illuminating the second fiberoptic cable with means for introducing light into said second fiberoptic cable to thereby cause said second cable to emit light from the tip thereof so that the first and second fiberoptic cables collectively illuminate the organic surroundings of a catheter guided to an intracorporeal location.

27. A method according to claim 26 wherein the step of coupling a second fiberoptic cable further comprises coupling said second elongate fiberoptic cable to the stylet body in substantially a parallel alignment therewith.

* * * * *

UNITED STATES PATENT AND TRADEMARK OFFICE
CERTIFICATE OF CORRECTION

PATENT NO. : 5,370,640
DATED : 12/06/94
INVENTOR(S) : Jack Kolff

It is certified that error appears in the above-indentified patent and that said Letters Patent is hereby corrected as shown below:

Column 9, Line 68:

insert the word --for-- before the word "insertion"

Column 10, Line 10:

delete the word "styler" and insert the word --stylet--

Column 10, Line 14:

delete the word "styler" and insert the word --stylet--

Column 10, Line 46:

delete the word "styler" and insert the word --stylet--

UNITED STATES PATENT AND TRADEMARK OFFICE
CERTIFICATE OF CORRECTION

PATENT NO. : 5,370,640
DATED : 12/06/94
INVENTOR(S) : Jack Kolff

It is certified that error appears in the above-indentified patent and that said Letters Patent is hereby corrected as shown below:

Column 12, Line 35:

delete the word "styler" and insert the word --stylet--.

Signed and Sealed this

Eighteenth Day of April, 1995

Attest:

BRUCE LEHMAN

*Commissioner of Patents and Trademarks*

*Attesting Officer*